United States Patent [19]

Fujimori et al.

[11] Patent Number: 4,933,344
[45] Date of Patent: Jun. 12, 1990

[54] ETHANONE OXIMES AND PHARMACEUTICAL COMPOSITIONS THEREOF

[75] Inventors: Shinichiro Fujimori, Yokohama; Satoshi Yamazaki, Machida; Mamoru Sugano, Kawasaki; Makoto Kawamura; Kunihiro Ninomiya, both of Machida; Akihiro Tobe, Yokohama; Issei Nitta, Machida, all of Japan

[73] Assignee: Mitsubishi Kasei Corporation, Japan

[21] Appl. No.: 239,169

[22] Filed: Aug. 31, 1988

[30] Foreign Application Priority Data

Sep. 3, 1987 [JP] Japan .................. 62-220877

[51] Int. Cl.$^5$ ................. A61K 31/495; C07D 241/04
[52] U.S. Cl. .................. 514/252; 514/225.5; 514/225.8; 514/253; 514/255; 514/316; 514/320; 514/321; 514/324; 514/325; 514/326; 514/331; 544/35; 544/39; 544/357; 544/360; 544/370; 544/378; 544/380; 544/398; 546/190; 546/196; 546/197; 546/202; 546/203; 546/210; 546/232
[58] Field of Search ............. 544/357, 360, 398, 370; 514/255, 256

[56] References Cited

U.S. PATENT DOCUMENTS 4,352,804 10/1982 van Zorge .................. 544/284 X

FOREIGN PATENT DOCUMENTS 55-19287 9/1980 Japan .

OTHER PUBLICATIONS

Buzas et al, Chemical Abstracts, vol. 79 (1973) 92278d.
Vejdelek et al, Chemical Abstracts, vol. 105 (1986) 11509s.

*Primary Examiner*—Richard L. Raymond
*Attorney, Agent, or Firm*—David G. Conlin; Patricia A. McDaniels

[57] ABSTRACT

Ethanone oximes represented by the following general formula:

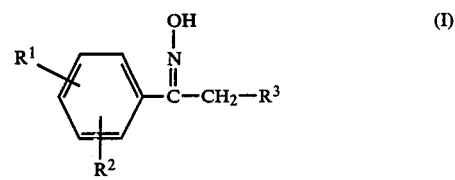

wherein
$R^1$ represents a cycloalkyl group, aryl group, aralkyl group, aryloxy group, aralkyloxy group, arylthio group or aryl sulfonyl group, those groups being optionally substituted with a substituent selected from an alkyl group having 1 to 3 carbon atoms, an alkoxy group having 1 to 3 carbon atoms and a halogen atom, piperidino group, piperazino group, 4-alkyl substituted piparazino group, imidazolyl group, 4-alkyl substituted imidazolyl group or substituted amino group,
$R^2$ represents a hydrogen atom or an alkoxy group having 1 to 3 carbon atoms, and
$R^3$ represents a piperidino group, piperazino group or 4-alkyl substituted piperazino group, or
$R^1$ and $R^2$ together with a phenyl group to which they are attached may form a phenothiazin-2-yl group, N-acetyl-phenothiazin-2-yl group, thianthren-2-yl group, dibenzothiophen-3-yl group, dibenzofuran-3-yl group or a group of the formula:

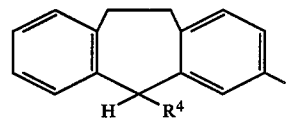

wherein $R^4$ represents a hydrogen atom or an alkyl group having 1 to 3 carbon atoms, or a pharmaceutically acceptable acid addition salts thereof are disclosed. They are a potent antiulcer agent.

2 Claims, No Drawings

ETHANONE OXIMES AND PHARMACEUTICAL COMPOSITIONS THEREOF

This invention relates to novel ethanone oximes. The ethanone oximes and pharmaceutically acceptable acid addition salts thereof according to the present invention have a potent antiulcer activity.

Heretofore, various compounds have been developed as an antiulcer agent. Among all, cimethidine which is a histamine $H_2$-blocker has recently been used extensively due to the excellent antiulcer activity hereof, but there has been pointed out that it involves several problems such as relapse. For instance, refer to Nikkei Medical, May 14, 1984, p 26–34.

The present inventors have made various studies while paying attention to oxime compounds in order to find out novel compounds of different chemical structure from that of the compounds known so far and having the potent antiulcer activity.

One of the oxime compounds of the antiulcer activity is an oxime ether derivative which is described in Japanese Patent Application Laid-Open (KOKAI) No. 55-19287. The present inventors have further made various studies for obtaining a compound showing a higher antiulcer activity and found that the object of the invention can be attained by novel ethanone oximes hereinunder described.

Specifically, the gist of the present invention lies in ethanone oximes represented by the following general formula I:

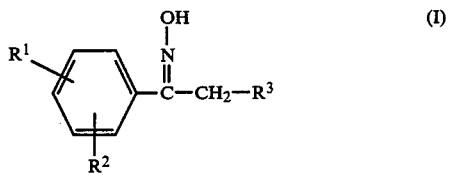

wherein $R^1$ represents a cycloalkyl group, aryl group, aralkyl group, aryloxy group, aralkyloxy group, arylthio group or aryl sulfonyl group, those groups being optionally substituted with a substituent selected from an alkyl group having 1 to 3 carbon atoms, an alkoxy group having 1 to 3 carbon atoms and a halogen atom, piperidino group, piperazino group, 4-alkyl substituted piperazino group, imidazolyl group, 4-alkyl substituted imidazolyl group or substituted amino group, $R^2$ represents a hydrogen atom or an alkoxy group having 1 to 3 carbon atoms, and $R^3$ represents a piperidino group, piperazino group or 4-alkyl substituted piperazino group, or $R^1$ and $R^2$ together with a phenyl group to which they are attached may form a phenothiazin-2-yl group, N-acetyl-phenothiazin-2-yl group, thianthren-2-yl group, dibenzothiophen-3-yl group, dibenzofuran-3-yl group or a group of the formula:

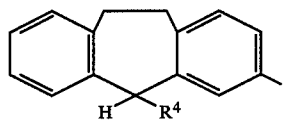

$R^4$ represents a hydrogen atom or an alkyl group having 1 to 3 carbon atoms, or a pharmaceutically acceptable acid addition salts thereof.

The present invention will be described more in detail hereinafter.

The ethanone oxime of the invention is depicted by the general formula I as described above. In the same formula I, $R^1$ represents a cycloalkyl group such as cyclohexyl or cyclopentyl group; an aryl group such as phenyl group; an aralkyl group such as benzyl or phenethyl group; an aryloxy group such as phenoxy group; an aralkyloxy group such as benzyloxy or phenethyloxy group; an arylthio group such as phenylthio group; or an aryl sulfonyl group such as phenylsulfonyl group. Those groups may optionally be substituted ith an alkyl group having 1 to 3 carbon atoms such as methyl group, ethyl group or propyl group, an alkoxy group having 1 to 3 carbon atoms such as methoxy group, ethoxy group or propoxy group, or a halogen atom such as chlorine atom or bromine atom.

Further, $R^1$ may represent a piperidino group such as 1-piperidino group; a piperazino group such as 1-piperazino group; 4-alkyl substituted piperazino group such as 4-methyl-1-piperazino group, 4-ethyl-1-piperazino group or 4-propyl-1-piperazino group; an imidazolyl group such as imidazol-1-yl group; or 4-alkyl substituted imidazolyl group such as 4-methylimidazol-1-yl group or 4-ethyl-imidazol-1-yl group.

Furthermore, $R^1$ may represent a substituted amino group such as phenylamino group, diphenylamino group, N-acetyl-anilino group, benzenesulfonyl amino group or p-toluenesulfonyl amino group.

$R^2$ represents a hydrogen atom or an alkoxy group having 1 to 3 carbon atoms such as methoxy group, ethoxy group or propoxy group. $R^3$ represents a piperidino group, piperazino group or a 4-alkyl substituted piperazino group such as 4-methyl-1-piperazino group, 4-ethyl-1-piperadino group or 4-propyl-1-piperadizino group.

Furthermore, $R^1$ and $R^2$ together with a phenyl group to which they are attached may form a phenothiazin-2-yl, N-acetyl-phenothiadin-2-yl, thianthren-2-yl group, dibenzothiophen-3-yl group, dibenzofuran-3-yl group or a group of the formula:

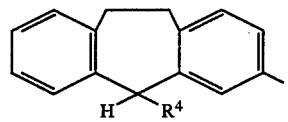

wherein $R^4$ represents a hydrogen atom or an alkyl group having 1 to 3 carbon atoms such as methyl, ethyl or propyl group.

As preferred compounds according to the present invention, there can be mentioned those compounds in which $R^1$ represents a cyclohexyl group, benzyl group, phenethyl group, benzyloxy group, phenylthio group or phenylsulfonyl group which may have the substituent as described above, or imidazol-1-yl group, diphenyl amino group, N-acetyl-anilino group or benzenesulfonyl amino group, or alternatively $R^1$ and $R^2$ may join to each other to represent, together with the phenyl group to which they are attached, a phenothiazin-2-yl group, N-acetyl-phenothiazin-2-yl group or a group of the formula:

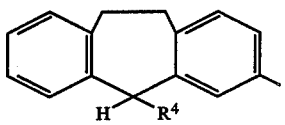

wherein R⁴ has the same meaning as described above, and R³ represents 1-piperidino group or 4-alkyl-1-piperazino group.

Particularly, those compounds in which R¹ substituted at the para-position of the phenyl ring are more preferred.

The preferred compounds in the present invention are specifically defined as below:

(Z)-2-(4-methylpiperazin-1-yl)-1-(4-phenylthio-phenyl)ethanone oxime, (Z)-2-(4-methylpiperazin-1-yl)-1-(4-cyclohexyl-phenyl)ethanone oxime, (Z)-2-(4-methylpiperazin-1-yl)-1-(4-benzyl-phenyl)-ethanone oxime, (Z)-2-(4-methylpiperazin-1-yl)-1-(4-(N-acetyl-N-phenylamino)-phenyl)-ethanone oxime, (Z)-2-(4-methylpiperazin-1-yl)-1-(4-diphenylamino-phenyl)ethanone oxime, (Z)-2-(4-methylpiperazin-1-yl)-1-(4-(2-phenylethyl)-phenyl)ethanone oxime, (Z)-2-(piperidin-1-yl)-1-(4-(2-phenylethyl)-phenyl)-ethanone oxime, (Z)-2-(4-methylpiperazin-1-yl)-1-(N-acetyl-phenothiazin-2-yl)ethanone oxime, (Z)-2-(4-piperidin-1-yl)-1-(N-acetyl-phenothiazin-2-yl)ethanone oxime, (E)-2-(4-methylpiperazin-1-yl)-1-(10,11-dihydro-5H-dibenzo[a, b]cyclohepten-3-yl)-ethanone oxime, (Z)-2-(4-methylpiperazin-1-yl)-1-(10,11-dihydro-5H-5-methyldibenzo[a,b]cyclohepten-3-yl)-ethanone oxime, (Z)-2-(4-methylpiperazin-1-yl)-1-(10,11-dihydro-5H-5-ethyldibenzo[a,b]cyclohepten-3-yl)-ethanone oxime, (Z)-2-(4-methylpiperazin-1-yl)-1-(4-phenylsulfonyl-phenyl)ethanone oxime, (Z)-2-(4-methylpiperazin-1-yl)-1-(phenothiazin-2-yl)-ethanone oxime, (Z)-2-(4-methylpiperazin-1-yl)-1-(4-(imidazol-1-yl)-phenyl)ethanone oxime, (Z)-2-(piperidin-1-yl)-1-(4-(imidazol-1-yl)-phenyl)-ethanone oxime, (Z)-2-(4-methylpiperazin-1-yl)-1-(4-benzenesulfonylamino-phenyl)-ethanone oxime, (Z)-2-(4-methylpiperazin-1-yl)-1-(4-benzyloxy-phenyl)ethanone oxime, (Z)-2-(4-methylpiperazin-1-yl)-1-(2-ethoxy-4-(2-phenylethyl)-phenyl)-ethanone oxime, and (Z)-2-(4-methylpiperazin-1-yl)-1-(4-(2-(2-isopropoxyphenyl)-ethyl)-phenyl)-ethanone oxime.

Acid addition salts of the ethanone oximes hereinbefore described are also included within the scope of the present invention.

As such acid addition salts, there can be mentioned those acid addition salts such as hydrochloride, hydrobromide, sulfate, phosphate, nitrate, acetate, succinate, adipate, propionate, tartarate, maleate, citrate, benzoate, toluenesulfonate and methanesulfonate.

A process of producing the compounds according to the present invention is to be described below.

The ethanone oximes of the invention represented by the general formula I may be prepared by converting an amino ketone of the formula II:

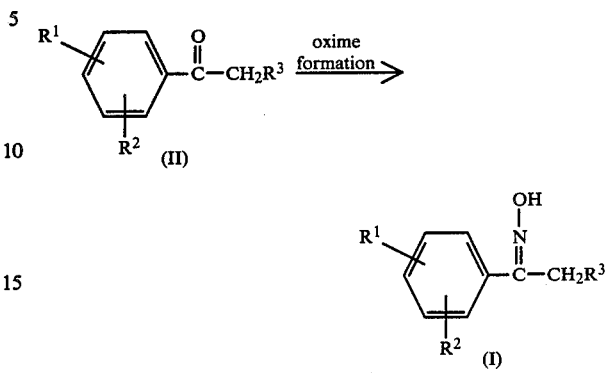

wherein R¹ to R³ are as defined in the general formula I into an oxime, i.e., hydroxyimination by a known method. A hydroxyl amine used for the oxime conversion may be in a free or hydrochloride form. The amount of the hydroxyl amine used is from 1 to 20 equivalents based on the compound (II).

The reaction may be conducted in an alcoholic solvent such as methanol or ethanol; an amide solvent such as dimethylformamide or N-methyl-2-pyrrolidinone; a sulfoxide solvent such as dimethylsulfoxide; an etheric solvent such as tetrahydrofuran or dioxane; a basic solvent such as pyridine or triethylamine; water; or a mixture of two or more of these solvents.

In the case of using the reagent of the hydroxyl amine in the form of hydrochloride, the reaction is usually taken place after adding an equimolar or more amount of tertiary amine such as pyridine, triethylamine, etc., or inorganic salt such as sodium hydroxide, potassium hydroxide, potassium carbonate or sodium carbonate to the solvent described above.

The reaction temperature is from −20° C. to 150° C. and, preferably, from 0° C. to 100° C.

While two kinds of Z-isomer and E-isomer may be prepared by the oxime-forming reaction as described above, the ethanone oxime (I) of the invention may be either in the form of a mixture of those two kinds of isomers or in the form of a single isomer after separating them into each of the isomers.

Usually, each of the two isomers can be obtained respectively by recovering the ethanone oxime (I) in the form of free base after the reaction and, thereafter, subjecting to conventional means such as recrystallization or column chromatography. If desired, the ethanone oximes of the general formula I can be obtained in the form of an acid addition salt by bringing them into contact with a desired acid.

The amino ketones represented by the formula II as the starting material for the reaction may be produced by each of following Methods-1 to 3.

(Method-1)

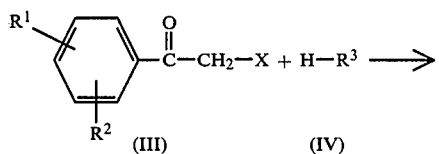

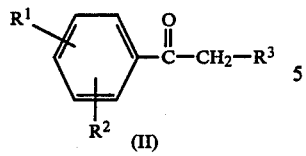

The symbols of $R^1$, $R^2$ and $R^3$ in this reaction formula are as defined in the general formula I and X is a halogen atom such as chlorine atom.

The amino ketones (II) may be obtained by reacting α-haloacetophenones (III) with amines (IV). Equimolar or more amount of the amines (IV) to the compounds (III) is usually used in the amination reaction above.

Although the reaction can be proceeded without solvent, it is possible to use those solvents inert to the reaction, for example, an etheric solvent such as dioxane or tetrahydrofuran; an amide solvent such as dimethylformamide or N-methyl-2-pyrrolidinone; an alcoholic solvent such as methanol or ethanol; water; or a mixture of two or more of them. There is no particular restriction for the reaction temperature, and it is usually from 0° C. to 150° C. Further, bases may be added for collecting a hydrogen halide formed by reaction, thereby promoting the reaction. As the bases, there can be mentioned, for example, inorganic bases such as sodium hydroxide, potassium hydroxide, sodium carbonate or potassium carbonate and tertiary amines such as pyridine or triethylamine. Equimolar or more amount of the bases to the compounds (III) is usually used. The desired amino ketones (II) may be obtained either in the form of a free base or in the form of the acid addition salt with hydrogen halide depending on the reaction conditions.

Since the reaction proceeds at a high yield, the thus obtained amino ketones (II) can be used for the oxime-forming reaction without further purification. Alternatively, the oxime-forming reaction may be conducted immediately after adding a hydroxylamine to a reaction mixture of amino ketones (II).

(Method-2)

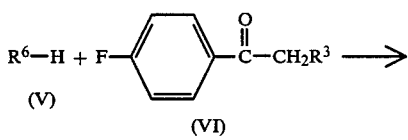

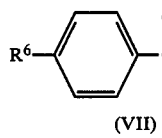

In this reaction formula, $R^3$ is as defined in the general formula I and $R^6$ is a imidazol-1-yl group, 4-methylimidazol-1-yl group, 1-piperidino group, 4-methyl-1-piperazino group or a group of

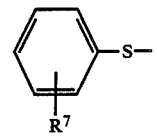

in which $R^7=$ —OMe, —CH$_3$ or —Cl.

Among the compounds of the formula II, those compounds (VII) may be obtained by reacting thiols or secondary amines (V) with a fluoride (VI). The reaction conditions may optionally be selected from two kind of methods hereinbelow mentioned.

In the first method, the reagents (V) and (VI) are reacted in an amide solvent such as dimethylformamide or N-methyl-2-pyrrolidinone in the presence of an inorganic salt such as potassium carbonate and a copper catalyst such as powdery copper. The reaction temperature is usually from 60° C. to 120° C.

The compound (V) is usually used in an equimolar or more amount to the fluoride (VI). The inorganic base such as potassium carbonate is used by 0.5 or more molar times of the amount of the fluoride (VI). Preferably, it is usually used in an amount from 1 to 3 molar times. The copper catalyst is used in an amount usually from 0.1 to 5% by weight of the fluoride (VI).

The second method is to react the reagents (V) and (VI) in an inert solvent such as dimethylsulfoxide in the presence of sodium hydride. Usually the reagent (V) is used in an equimolar or more amount to the fluoride (VI). Sodium hydride is usually used by from 1 to 3 molar times of the reagent (V). The reaction temperature is usually from room temperature to 120° C.

The starting material (VI) may be obtained by reacting amines (IV) and 4-fluoro-α-haloacetophenone under the conditions as described in Method-1 above.

(Method-3)

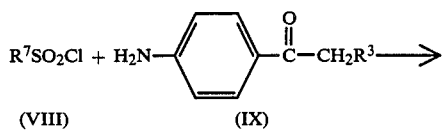

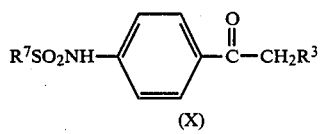

In this reaction formula, $R^3$ is as defined in the general formula I and $R^7$ is a phenyl group or toluyl group.

Among the compounds of the general formula II, those compounds (X) may be obtained by reacting sulfonyl chlorides (VIII) and anilines (IX) under the conventionally known conditions.

That is, it can be conducted by dissolving the anilines (IX) into a solvent of pyridine and thereafter adding the sulfonyl chloridse (VIII) thereto under ice cooling.

The anilines (IX) as the starting material may be obtained by reacting the compound (IV) and 4-acetylamino-α-haloacetophenone by the method as described in Method-1 and then hydrolyzing a reaction product by a conventional method.

The α-haloacetophenones of the formula III as the starting material in the reaction of Method-1 can be prepared by any one of the following processes depending on the properties of $R^1$ and $R^2$.

(A) Friedel-Crafts reaction of an aromatic compound with a haloacetylhalide

It may be carried out in line with the method as described in G. Cavarrini, et al., J. Med. Chem., 6, 573-578 (1963). This process is applicable to α-haloacetophenones as described in Examples 1-19 hereinafter described.

(B) Conversion of α-haloacetophenone derivatives a. Oxidation of sulfide to sulfoxide It may be carried out in line with the method as described in G. Cavarrini, et al., J. Med. Chem., 6, 573-578 (1963). This process is applicable to α-haloacetophenone as described in Example 20 hereinafter described.

b. Hydrolysis of N-acetylated derivative

This process is applicable to α-haloacetophenones as described in Examples 21 and 22 hereinafter described.

(C) α-halogenation of acetophenones

This process is applicable to α-haloacetophenones as described in Examples 33-44 hereinafter described.

The acetophenones of the starting material for the process (C) above can be prepared in a known method, for instance, by the reaction between a Grignard reagent of Example 35 and anhydrous acetic acid or by Fries rearrangement of phenylacetate in Example 34.

The pharmacological effect of the ethanone oximes and acid addition salts thereof according to the present invention will be described hereinunder based on the results of inhibiting effects of stress-induced gastric ulcer in rats. Anti-stress ulcer tests were conducted as described below.

Douryu non-fasted male rats (Shizuoka Laboratory Animal Center, body weight: 220-250 g), five in each group, were immobilized within a stress cage made of wire net and immersed in a water bath at 22°±1° C. to a depth of xiphoid for loading them with stresses. The rats were clubbed to death after 15 hours and their stomachs were extirpated. After injecting about 15 ml of an aqueous 1% formalin solution into each of the stomachs, they were immersed in an aqueous 1% formalin solution for about 10 minutes and fixed. After fixation, the stomachs were incised along the greater curvature. The longer diameter of each ulcer generated in the glandular portion was measured under stereomicroscope (X10) and the sum of them was defined to be an ulcer coefficient (mm). Chemicals to be tested were suspended in an aqueous 1% gum arabic solution and orally administrated at a dose of 2 ml/kg, 30 min before the stress loading. For the control group, an aqueous 1% gum arabic solution only was administrated, and their ulcer coefficient was compared to that of the group administrated with the tested chemicals to calculate the suppression rate of the tested chemicals. The dosage was 50 mg/kg for each of the compounds.

The test results are shown in Table-1 below. The test compounds in the table are identified in corresponding Examples hereinafter described.

TABLE-1

| Test Compound (Example No.) | Oxime Isomer | Inhibition Rate of Stress-Induced Ulcer (%) |
|---|---|---|
| 1* | Z | 76.9 |
| 3 | Z | 59.7 |
| 5 | Z | 100.0 |
| 6 | Z | 85.7 |
| 7 | Z | 74.6 |
| 8 | Z | 65.7 |
| 11 | Z | 53.0 |
| 13 | Z | 100.0 |
| 14 | Z | 51.9 |
| 17 | E | 78.0 |
| 18 | Z | 100.0 |
| 19 | Z | 90.7 |
| 20 | Z | 80.3 |
| 22 | Z | 50.6 |
| 23 | Z | 50.5 |
| 24 | Z | 41.5 |
| 31 | Z | 48.4 |
| 33 | Z | 41.4 |
| 34 | Z | 100.0 |
| 40 | Z | 41.9 |
| Cimethidine | | 69.7** |

*This compound is in the form of hydrochloride.
**200 mg/kg. P.O.

As apparent from the results of the test, the ethanone oximes and acid addition salts thereof according to the present invention are useful as an antiulcer agent.

The ethanone oximes and acid addition salts thereof according to the invention can be administered for therapy of ulcer through any route. That is, not only parenteral administration such as subcutanous injection, intravenous injection, intramuscular injection, intraabdominal injection, etc. but oral administration may be acceptable.

The dosage may be determined depending on the age, state of health, body weight or stage of ulcer of a patient and further taking into consideration the frequency of the treatment, the kind of a treatment applied simultaneously, if any, and the degree of desired effect.

Generally, the dosage of the effective ingredient per one day is from 0.1 to 10 mg/kg body weight and, usually, from 0.3 to 5 mg/kg body weight, and it may be administrated once or more times in one day.

The compounds of the invention may be formulated for the oral administration into, for instance, tablet, capsule, powder, solution or elixir, and for parenteral administration they may be formulated into a sterilized liquid form such as solution or suspension. A non-toxic solid or liquid pharmaceutical carrier may be incorporated into the pharmaceutical composition according to the invention.

As the example of the solid carrier, gelatin type capsules are usually used. Further, any adjuvant may be incorporated into the tablet or powder formulation.

These capsule, tablet and powder usually contain the effective ingredient from 5 to 95% and, preferably, from 25 to 90% by weight.

That is, it is preferred that the effective ingredient is contained by from 5 to 500 mg and, preferably, from 5 to 100 mg in these formulations.

As the liquid carrier, water, petroleum, oils of animal or plant origin such as peanuts oil, soybean oil, mineral oil and sesame oil or synthetic oil may, be used.

Further, physiological saline solution, solution of dextrose or other similar saccharide, and glycols such as ethylene glycol, propylene glycol or polyethylene glycol are generally preferred as the liquid carrier and, particularly, in the case of an injection solution using physiological saline solution, it contains the effective ingredient usually from 0.5 to 20% and, preferably, from 1 to 10% by weight.

In the case of the liquid oral administration, a liquid suspension or syrup containing from 0.5 to 10% by weight of the effective ingredient is preferred. As the carrier in this case, water-like vehicle such as perfume, syrup or pharmaceutical micelle body is preferred.

As has been described above specifically, the ethanone oximes and acid addition salts thereof according to the present invention are novel compounds and useful as the antiulcer agent.

The present invention will be explained more in detail referring to Examples, but the invention is not restricted to the following Examples unless it exceeds the gist of the present invention.

EXAMPLE 1

2-(4-Methylpiperazin-1-yl)-1-(4-phenylthio-phenyl)ethanone oxime

After dissolving 10.0 g of 4-chloroacetyldiphenylsulfide into 50 ml of methanol, 7.7 g of N-methylpiperazine was added and stirred at a room temperature for one hour and subsequently under reflux for two hours. After cooling to the room temperature, 5.3 g of hydroxylamine hydrochloride was added and stirred for one hour followed by being left over one night. Then, the reaction solution was concentrated to solid, and thereafter chloroform and an aqueous saturated solution of potassium carbonate were added to the residue under cooling to separate liquid layers. After washing the organic layer with water, and being dried over anhydrous sodium sulfate, it was concentrated to obtain a mixture of Z-isomer and E-isomer. Then, the mixture was separated by silica gel column chromatography using chloroform/methanol (97:3) as an elute and then recrystallized respectively from ethanol to obtain 6.6 g of (Z)-2-(4-methylpiperazin-1-yl)-1-(4-phenylthiophenyl)ethanone oxime with melting point of from 189° to 190° C. and 2.5 g of (E)-2-(4-methyl-piperazin-1-yl)-1-(4-phenylthio-phenyl)-ethanone oxime with the melting point of from 168° to 169° C.

The acid addition was conducted as described below.

After dissolving 3.0 g of the Z-isomer into 180 ml of ethanol under heating and then cooling, 1.1 ml of a solution of 30% hydrochloric acid - ethanol was added at a room temperature under stirring.

Then, ethanol was concentrated to about ½ under a reduced pressure and then stirred under ice-cooling for one hour. The deposited crystals were collected by filtration and dried to obtain 3.1 g of (Z)-2-(4-methyl-piperazin-1-yl)-1-(4-phenylthio-phenyl)-ethanone oxime hydrochloride with the melting point of from 217° to 219° C. (decomposition).

EXAMPLES 2 to 19

The compounds in Tables-2 and 3 were prepared in line with the procedures of Example 1.

TABLE 2

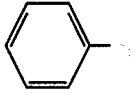

| Example No. | R¹ | R³ | Oxime Isomer | Addition Salt | Melting Point |
|---|---|---|---|---|---|
| 2 | 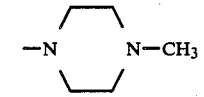 | −N(piperazine)N−CH₃ | Z | HCl | 225–228° C. (decomposition) |
| 3 | 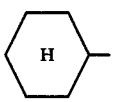 | " | " | free base | 196–198° C. |
| 4 | 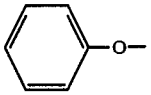 | " | " | " | 173–174° C. |
| 5 | 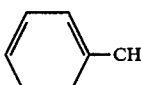 | " | " | " | 180–182° C. |
| 6 | 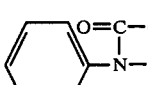 | " | " | " | 207–208° C. |

TABLE 2-continued $$R^1-\underset{\underset{\|}{C}}{\overset{\overset{OH}{|}}{\underset{N}{\|}}}-CH_2-R^3$$ (on phenyl ring)

| Example No. | R¹ | R³ | Oxime Isomer | Addition Salt | Melting Point |
|---|---|---|---|---|---|
| 7 | diphenylamino (Ph₂N–) | " | " | " | 214–215° C. (decomposition) |
| 8 | PhCH₂CH₂– | " | " | HCl | 175–182° C. (decomposition) |
| 8' | " | " | E | " | 198–200° C. |
| 9 | " | –N(piperazinyl)N–C₂H₅ | Z | " | 191–192° C. |
| 10 | " | –N(piperazinyl)N–C₃H₇ | " | " | 187–190° C. (decomposition) |
| 11 | " | –N(piperidinyl) | " | free base | 120–122° C. |

TABLE 3

$$R-\underset{\underset{\|}{C}}{\overset{\overset{OH}{|}}{\underset{N}{\|}}}-CH_2-R^3$$

| Example No. | R | R³ | Oxime Isomer | Addition Salt | Melting Point |
|---|---|---|---|---|---|
| 12 | 10-acetylphenothiazin-2-yl (O=C-CH₃ on N of phenothiazine) | –N(piperazinyl)N–CH₃ | Z | free base | 199–200° C. |
| 12' | " | " | E | " | 122–124° C. |
| 13 | " | –N(piperidinyl) | Z | " | 192–193° C. |
| 14 | dibenzo[b,e][1,4]dithiin-2-yl | –N(piperazinyl)N–CH₃ | " | " | 214–215° C. |

TABLE 3-continued $$R-\underset{\underset{\underset{OH}{|}}{\overset{N}{\|}}}{C}-CH_2-R^3$$

| Example No. | R | R³ | Oxime Isomer | Addition Salt | Melting Point |
|---|---|---|---|---|---|
| 15 | dibenzothiophene-yl | " | " | " | 184–185° C. |
| 16 | dibenzofuran-yl | " | " | " | 193–195° C. |
| 17 | 10,11-dihydro-5H-dibenzo[a,d]cycloheptene-yl | " | Z | HCl | 195–207° C. (decomposition) |
| 17' | " | " | E | " | 187–194° C. (decomposition) |
| 18 | 5-methyl-10,11-dihydro-5H-dibenzo[a,d]cycloheptene-yl | " | Z | " | 180–187° C. (decomposition) |
| 18' | " | " | E | " | 159–165° C. (decomposition) |
| 19 | 5-ethyl-10,11-dihydro-5H-dibenzo[a,d]cycloheptene-yl | " | Z | " | 160–175° C. (decomposition) |

EXAMPLE 20

(Z)-2-(4-methylpiperazin-1-yl)-1-(4-phenylsulfonylphenyl)-ethanone oxime

Using 10.0 g of 4-chloroacetyldiphenylsulfoxide, 6.3 g of (Z)-2-(4-methylpiperazin-1-yl)-1-(4-phenylsulfonylphenyl)-ethanone oxime with the melting point of from 212°–213° C. was obtained in the same manner as in Example 1.

EXAMPLE 21

(Z)-2-(4-methylpiperazin-1-yl)-1-(4-phenylaminophenyl)-ethanone oxime

After dissolving 10.0 g of 2-chloro-1-(4-(N-acetyl-N-phenyl-amino)-phenyl)-ethanone into 100 ml of acetic acid, 40 ml of concentrated hydrochloric acid was added and then refluxed by heating for 4 hours under stirring in a nitrogen atmosphere. After cooling, the reaction solution was poured into water, and deposited crystals were collected by filtration, washed with water and dried to obtain 6.5 g of 2-chloro-1-(4-phenyl-aminophenyl)-ethanone. Then, using 6.5 g of the thus obtained chloride, 3.3 g of (Z)-2-(4-methylpiperazin-1-yl)-1-(4-phenylaminophenyl)-ethanone oxime with the melting point of from 196° to 197° C. was obtained in the same manner as in Example 1.

EXAMPLE 22

(Z)-2-(4-methylpiperazin-1-yl)-1-(4-phenothiazin-2-yl)-ethanone oxime

The titled compound was synthesized in the same manner as in Example 21.

Melting point: 216°–218° C.

EXAMPLE 23

(Z)-2-(4-methylpiperazin-1-yl)-1-(4-(imidazol-1-yl)phenyl)-ethanone oxime 5.2 g of imidazole was added to 3.6 g of 50% sodium hydride in oil in 50 ml of dimethylsulfoxide at room temperature under stirring in a nitrogen atmosphere. After stirring at the room temperature for 30 min, 6.0 g of 2-(4-methylpiperazin-1-yl)-1-(4-fluorophenyl)-ethanone dissolved in 30 ml of dimethylsulfoxide was dropped followed by stirred at 100° C. for one hour. After cooling, the reaction solution was poured into iced water, extracted with chloroform, washed with water, dried over anhydrous sodium sulfate and then further concentrated to solid. 50 ml of methanol and 7 ml of triethylamine were added to the residue and, after dissolving, 3.5 g of hydroxylamine hydrochloride was added. Then, in the same manner as in Example 1, 2.5 g of (Z)-2-(4-methylpiperazin-1-yl)-1-(4-(imidazol-1-yl)-phenyl)-ethanone oxime with the melting point of from 199° to 200° C. was obtained.

EXAMPLES 24 to 27

The compounds in Table-4 were prepared in line with the procedures of Example 23.

TABLE 4

$$R^1-\text{C}_6\text{H}_4-\underset{\underset{\text{OH}}{\|}}{\text{C}}(\text{=N-OH})-\text{CH}_2-R^3$$

| Example No. | R¹ | R³ | Oxime Isomer | Addition Salt | Melting Point |
|---|---|---|---|---|---|
| 24 | imidazol-1-yl | piperidin-1-yl | Z | free base | 138–142° C. |
| 25 | 2-methylimidazol-1-yl | 4-methylpiperazin-1-yl | " | " | 161–164° C. |
| 26 | piperidin-1-yl | " | " | " | 192–194° C. |
| 27 | 4-methylpiperazin-1-yl | " | " | " | 168–170° C. |

EXAMPLE 28

(Z)-2-(4-methylpiperazin-1-yl)-1-(4-(4-methoxy-phenylthio)-phenyl)-ethanone oxime 5.4 g of 4-methoxybenzenethiol, 5.3 g of anhydrous potassium carbonate, 0.06 g of copper powder and 20 ml of dimethylformamide were added to 6.0 g of 2-(4-methyl-piperazin-1-yl)-1-(4-fluoro-phenyl)-ethanone and stirred at 110° C. in a nitrogen atmosphere for 2 hours.

After cooling, the reaction solution was poured into iced water, extracted with chloroform, washed with water, dried over anhydrous sodium sulfate and then concentrated to solid. The residue was dissolved in 50 ml of methanol and 7 ml of triethylamine and then 3.5 g of hydroxylamine hydrochloride was added. Then, in the same manner as in Example 1, 3.4 g of (Z)-2-(4-methyl-piperazin-1-yl)-1-(4-(4-methoxy-phenylthio)-phenyl)-ethanone oxime with the melting point of from 176°–178° C. was obtained.

EXAMPLES 29 and 30

The compounds in Table-5 were prepared in line with the procedures of Example 28.

TABLE 5

$$R^1-\text{C}_6\text{H}_4-\underset{\underset{\text{OH}}{\|}}{\text{C}}(\text{=N-OH})-\text{CH}_2-\text{N}(4\text{-methylpiperazin-1-yl})$$

| Example No. | R¹ | Oxime Isomer | Addition Salt | Melting Point |
|---|---|---|---|---|
| 29 | 4-chlorophenylthio | Z | HCl | 181–182° C. |
| 30 | 4-methylphenylthio | " | " | 214–218° C. (decomposition) |

EXAMPLE 31

(Z)-2-(4-methylpiperazin-1-yl)-1-(4-benzenesulfonylamino-phenyl)-ethanone oxime 1.8 g of sodium hydroxide dissolved in 10 ml of ethanol and 10 ml of water were added to 4.0 g of 2-(4-methylpiperazin-1-yl)-1-(4-acetylamino-phenyl)-ethanone which was obtained in the same manner as in Example 1, and stirred at 85° C. for 2 hours in a nitrogen atmosphere. Then, ethanol was distilled off, the deposited oily product was extracted with chloroform, washed with water, dried over anhydrous sodium sulfate and further concentrated to solid to obtain 2.7 g of 2-(4-methylpiperazin-1-yl)-1-(4-aminophenyl)-ethanone.

Then, 16 ml of pyridine was added to 2.7 g of the thus obtained amino compound and then 2.1 g of benzenesulfonyl chloride was added under ice cooling while stirring. Then, after stirring at room temperature for 3 hours, 1.6 g of hydroxyl amine hydrochloride was added. Then, in the same manner as in Example 1, 2.2 g of (Z)-2-(4-methylpiperazin-1-yl)-1-(4-benzenesulfonyl amino-phenyl)-ethanone oxime with the melting point of from 196° to 199° C. (decomposition) was obtained.

EXAMPLE 32

(Z)-2-(4-methylpiperazin-1-yl)-1-(4-(p-toluenesulfonyl-amino)-phenyl)-ethanone oxime The titled compound was synthesized in the same manner as in Example 31.

mp: 192°–193° C.

EXAMPLE 33

2-(4-Methylpiperazino-1-yl)-1-(4-benzyloxy-phenyl)ethanone oxime hydrochloride

After dissolving 4.0 g of 4-benzyloxyacetophenone into 20 ml of 1,4-dioxane and 20 ml of tetrahydrofuran, 0.1 g of anhydrous aluminum chloride and 3.1 g of bromine were added under ice cooling and stirring. Further, after stirring for 5 hours under ice cooling, the reaction solution was concentrated to solid. Water and chloroform were added to the residue to separate liquid layers. Then, the chloroform layer was dried over anhydrous sodium sulfate and then concentrated to solid followed by purification by silica gel column chromatography using benzene/n-hexane (1:1) as an elute, to obtain 4.1 g of 2-bromo-1-(4-benzyloxy-phenyl)-ethanone. Then, using 3.0 g of the thus obtained bromide, 2.2 g of (Z)-2-(4-methyl-piperazin-1-yl)-1-(4-benzyloxy-phenyl)-ethanone oxime hydrochloride with the melting point of from 208° to 210° C. (decomposition) and 0.7 g of (E)-2-(4-methyl-piperazin-1-yl)-1-(4-benzyloxy-phenyl)-ethanone oxime hydrochloride with the melting point of from 210° to 212° C. were obtained in the same manner as in Example 1.

EXAMPLE 34

(Z)-2-(4-methylpiperazin-1-yl)-1-(2-ethoxy-4-(2-phenylethyl)-phenyl)-ethanone oxime hydrochloride 40 ml of nitrobenzene and 7.2 g of anhydrous aluminum chloride were added to 10.0 g of 3-(2-phenylethyl-)acetoxybenzene and stirred at 130° C. for 30 min in a nitrogen atmosphere. After cooling, the reaction solution was poured into a mixture of ice and hydrochloric acid, extracted with chloroform, washed with water, dried over anhydrous sodium sulfate and then concentrated to solid. The residual was purified by silica gel column chromatography using benzene/n-hexane (1:1) as an elute, to obtain 8.3 g of 1-(2-hydroxy-4-(2-phenylethyl)-phenyl)-ethanone as an oily product. Then, by using 8.3 g of the hydroxyl compound, 5.4 g of 2-(4-methylpiperazin-1-yl)-1-(2-hydroxy-4-(2-phenylethyl)-phenyl)-ethanone was obtained in the same manner as in Example 33.

Then, after dissolving 5.4 g of the latter hydroxyl compound into 100 ml of toluene, 3.2 g of potassium hydroxide and 0.6 g of tetrabutyl ammonium bromide dissolved in 50 ml of water were added and stirred at room temperature for 30 min in a nitrogen atmosphere. Then, 3.7 g of diethylsulfate was added and stirred at 90° C. for 3 hours. After cooling, the solution was separated, and the toluene layer was washed with water, dried over anhydrous sodium sulfate and 3.2 ml of a solution of 20% hydrochloric acid-ethanol was added. The deposited crystals were collected by filtration and recrystallized from 2-propanol to obtain 3.6 g of 2-(4-methylpiperazin-1-yl)-1-(2-ethoxy-4-(2-phenylethyl)-phenyl)-ethanone dihydrochloride with the melting point of from 163° to 166° C. Then, after dissolving 3.6 g of the ethanone into 100 ml of methanol, 5 ml of triethylamine and 1.7 g of hydroxylamine hydrochloride were added and, in the same manner as in Example 1, 1.5 g of (Z)-2-(4-methylpiperazin-1-yl)-1-(2-ethoxy-4-(2-ethanone oxime hydrochloride with the melting point of from 206° to 209° C. (decomposition) was obtained.

EXAMPLE 35

2-(4-Methylpiperazin-1-yl)-1-(3-(2-phenylethyl)-phenyl)-ethanone oxime

A Grignard compound synthesized from 1.0 g of magnesium and 10.0 g of 3-(2-phenylethyl)-bromobenzene in 30 ml of tetrahydrofuran was dropped at −60° C. under stirring for 3 min into 7.6 g of anhydrous acetic acid dissolved in 20 ml of tetrahydrofuran in a nitrogen atmosphere and stirred for further one hour. Then, the reaction solution was poured into a mixture of ice and an aqueous saturated solution of ammonium chloride and extracted with toluene. After separating the solution, it was washed with an aqueous 2N-solution of sodium hydroxide and saturated saline solution successively, dried over anhydrous sodium sulfate and then concentrated to solid. The residue was purified by silica gel column chromatography, using benzene/n-hexane (1:1) as an elute, to obtain 7.9 g of 1-(3-(2-phenylethyl)-phenyl)ethanone as an oily product. Then, by using 5.0 g of the thus obtained acetophenone compound, 3.8 g of (Z)-2-(4-methylpiperazin-1-yl)-1-(3-(2-phenylethyl)-phenyl-ethanone oxime hydrochloride with the melting point of from 185° to 188° C. (decomposition) and 0.5 g of (E)-2-(4-methylpiperazin-1-yl)-1-(3-(2-phenylethyl)-phenyl)-ethanone oxime with the melting point from 133° to 134° C. were obtained in the same manner as in Example 33.

EXAMPLES 36 TO 44′

The compounds in Table-6 were prepared in line with the procedures of Example 35.

TABLE 6

$$\underset{R-\underset{\|}{C}-CH_2-N}{\overset{OH}{\overset{|}{N}}}\underset{}{\bigg\langle} \underset{}{\bigg\rangle} N-CH_3$$

| Example No. | R | Oxime Isomer | Addition Salt | Melting Point |
|---|---|---|---|---|
| 36 | C₆H₅—CH₂CH₂—(2-methylphenyl) | Z | HCl | 178–185° C. (decomposition) |
| 36' | " | E | " | 178–182° C. (decomposition) |
| 37 | 4-CH₃—C₆H₄—CH₂CH₂—C₆H₄— | Z | " | 208–210° C. (decomposition) |
| 38 | 2-CH₃O—C₆H₄—CH₂CH₂—C₆H₄— | " | " | 193–200° C. (decomposition) |
| 38' | " | E | " | 160–185° C. (decomposition) |
| 39 | 2-C₂H₅O—C₆H₄—CH₂CH₂—C₆H₄— | Z | " | 186–190° C. (decomposition) |
| 39' | " | E | " | 169–178° C. (decomposition) |
| 40 | 2-(CH₂)₃CH—O—C₆H₄—CH₂CH₂—C₆H₄— | Z | HCl | 179–183° C. (decomposition) |
| 40' | " | E | " | 150–158° C. (decomposition) |
| 41 | 3-CH₃O—C₆H₄—CH₂CH₂—C₆H₄— | Z | " | 170–173° C. (decomposition) |
| 42 | 3-(CH₃)₂CH—O—C₆H₄—CH₂CH₂—C₆H₄— | " | " | 135–137° C. |
| 43 | 3-biphenyl— | " | " | 198–200° C. |

TABLE 6-continued $$\underset{R-\overset{\|}{C}-CH_2-N}{\overset{OH}{\underset{|}{N}}} \underset{\diagdown \diagup}{\diagup \diagdown} N-CH_3$$

| Example No. | R | Oxime Isomer | Addition Salt | Melting Point |
|---|---|---|---|---|
| 44 | 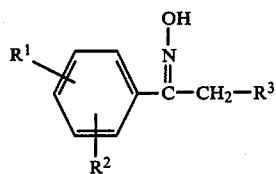 | " | 2HCl | 145–147° C. |
| 44' |  | E | " | 146–148° C. |

What is claimed is:

1. Ethanone oximes represented by the following general formula I:

$$R^1 \underset{R^2}{\diagdown} \underset{}{\bigcirc} \underset{\overset{\|}{C}-CH_2-R^3}{\overset{OH}{\underset{|}{N}}} \quad (I)$$

wherein
R[1] represents a cycloalkyl group, aryl group, aralkyl group, aryloxy group, aralkyloxy group, arylthio group or aryl sulfonyl group, those groups being optionally substituted with a substituent selected from an alkyl group having 1 to 3 carbon atoms, an alkoxy group having 1 to 3 carbon atoms and a halogen atom, piperidino group, piperazino group, 4-alkyl substituted piperazino group, imidazolyl group, 4-alkyl substituted imidazolyl group or substituted amino group, R[2] represents a hydrogen atom or an alkoxy group having 1 to 3 carbon atoms, and wherein R[1] and R[2] do not form a fused ring, and R[3] represents a piperazino group or 4-alkyl substituted pieprazino group, or a pharmaceutically acceptable acid addition salt thereof.

2. A pharmaceutical composition having an antiulcer activity, comprising as a main ingredient ethanone oximes represented by the following general formula I:

$$R^1 \underset{R^2}{\diagdown} \underset{}{\bigcirc} \underset{\overset{\|}{C}-CH_2-R^3}{\overset{OH}{\underset{|}{N}}} \quad (I)$$

wherein
R[1] represents a cycloalkyl group, aryl group, aralkyl group, aryloxy group, aralkyloxy group, arylthio group or aryl sulfonyl group, those groups being optionally substituted with a substituent selected from an alkyl group having 1 to 3 carbon atoms, an alkoxy group having 1 to 3 carbon atoms and a halogen atom, piperidino group, piperazino group, 4-alkyl substituted piperazino group, imidazoyl groups, 4-alkyl substituted imidazolyl group or substituted amino group, R[2] represents a hydrogen atom or an alkoxy group having 1 to 3 carbon atoms, and wherein R[1] and R[2] do not form a fused ring, and R[3] represents piperazino group or 4-alkyl substituted piperazino group, or a pharmaceutically acceptable acid addition salt thereof, in combination with a pharmaceutically acceptable diluent or carrier.

* * * * *